United States Patent
Ihara et al.

(10) Patent No.: US 8,310,668 B2
(45) Date of Patent: *Nov. 13, 2012

(54) PRODUCING METHOD OF WIRED CIRCUIT BOARD

(75) Inventors: Terukazu Ihara, Osaka (JP); Yoshihiro Toyoda, Osaka (JP)

(73) Assignee: Nitto Denko Corporation, Osaka (JP)

( * ) Notice: Subject to any disclaimer, the term of this patent is extended or adjusted under 35 U.S.C. 154(b) by 346 days.

This patent is subject to a terminal disclaimer.

(21) Appl. No.: 12/656,755

(22) Filed: Feb. 16, 2010

(65) Prior Publication Data

US 2010/0208250 A1    Aug. 19, 2010

(30) Foreign Application Priority Data

Feb. 17, 2009  (JP) ................................ 2009-034225

(51) Int. Cl.
  *G01N 21/88* (2006.01)
  *H05K 3/00* (2006.01)
(52) U.S. Cl. ............... 356/237.4; 356/237.1; 356/237.2; 356/237.3; 356/237.5; 29/829
(58) Field of Classification Search .... 356/237.1–237.5; 250/562, 563; 430/30, 311; 29/850, 829, 29/830, 831, 832
See application file for complete search history.

(56) References Cited

U.S. PATENT DOCUMENTS

| | | | |
|---|---|---|---|
| 4,970,368 A | | 11/1990 | Yamazaki et al. |
| 5,278,012 A | * | 1/1994 | Yamanaka et al. ............... 430/30 |
| 6,014,209 A | * | 1/2000 | Bishop ....................... 356/237.5 |
| 6,084,664 A | | 7/2000 | Matsumoto et al. |
| 7,561,434 B2 | * | 7/2009 | Nakamura et al. ............ 361/750 |
| 2005/0260391 A1 | * | 11/2005 | Nakamura et al. ............ 428/209 |
| 2009/0113704 A1 | * | 5/2009 | Toyoda ......................... 29/850 |
| 2009/0114426 A1 | | 5/2009 | Tsunekawa et al. |

FOREIGN PATENT DOCUMENTS

| | | |
|---|---|---|
| JP | 11-307883 | 11/1999 |
| JP | 2006-112845 | 4/2006 |
| JP | 2008-153595 | 7/2008 |

* cited by examiner

*Primary Examiner* — Sang Nguyen
(74) *Attorney, Agent, or Firm* — Jean C. Edwards, Esq.; Edwards Neils PLLC

(57) ABSTRACT

A producing method of a wired circuit board includes the steps of applying light from above the wired circuit board toward the wired circuit board, and sensing pattern reflected light which is the light reflected by a conductive pattern, table reflected light which is the light reflected by a support table via an insulating layer exposed from the conductive pattern, and foreign-matter reflected light which is the light reflected by a foreign matter present on the insulating layer to inspect the conductive pattern and the foreign matter based on a contrast therebetween. A reflectance of the table reflected light is in a range of 30 to 70%, and a reflectance of the foreign-matter reflected light is in a range of not more than 10%.

3 Claims, 6 Drawing Sheets

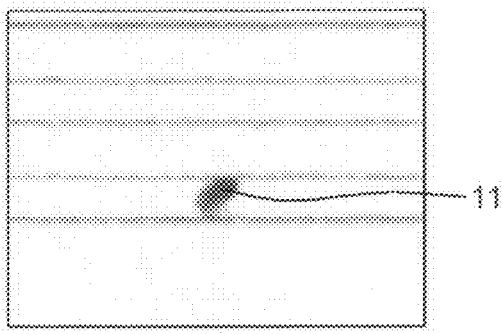
FIG. 9 COMPARATIVE EXAMPLE 1
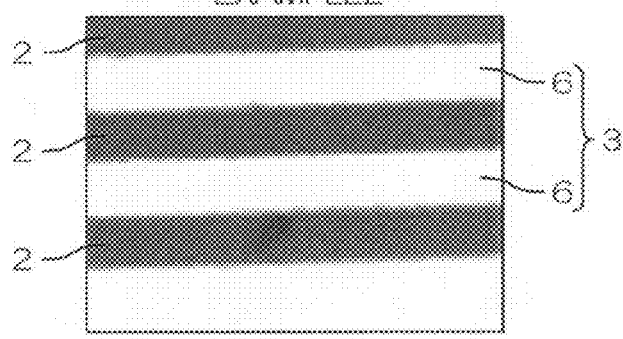
FIG. 10 COMPARATIVE EXAMPLE 2
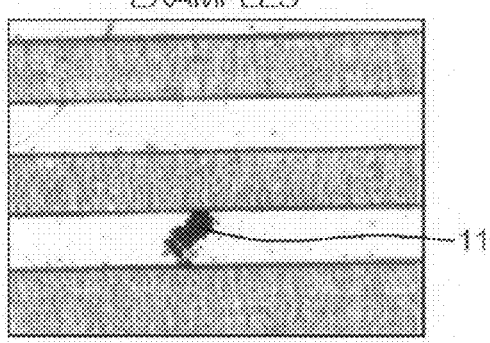
FIG. 11 COMPARATIVE EXAMPLE 3
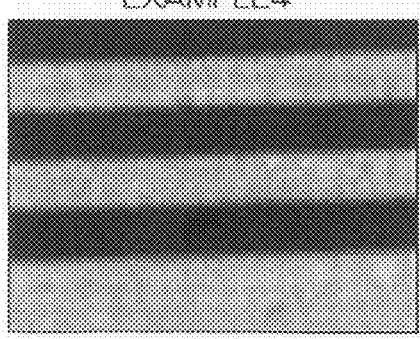
FIG. 12 COMPARATIVE EXAMPLE 4

PRODUCING METHOD OF WIRED CIRCUIT BOARD

CROSS REFERENCE TO RELATED APPLICATION

The present application claims priority from Japanese Patent Application No. 2009-034225 filed on Feb. 17, 2009, the content of which is hereby incorporated by reference in its entirety.

BACKGROUND OF THE INVENTION

1. Field of the Invention

The present invention relates to a producing method of a wired circuit board and, more particularly, to a producing method of a wired circuit board such as a flexible wired circuit board.

2. Description of the Related Art

A wired circuit board such as a flexible circuit board has an insulating base layer and a conductive pattern formed thereon. It has been known that, in the production of such a wired circuit board, a conductive pattern is formed on an insulating base layer, and then the shape of the conductive pattern is optically inspected for a defect.

For example, as shown in FIG. 5, it has been proposed that a wired circuit board 40 including an insulating base layer 42 and a conductive pattern 41 formed thereon is placed on the upper surface of a support table 44 made of metal, and then light is applied to the wired circuit board 40 from thereabove to effect an inspection of the conductive pattern 41 with reflected light which is the light reflected by the wired circuit board 40 (see, e.g., Japanese Unexamined Patent No. 2006-112845).

Specifically, pattern reflected light 51 which is the light reflected by the conductive pattern 41 and table reflected light 52 which is the light reflected by the support table 44 via the insulating base layer 42 exposed from the conductive pattern 41 are each sensed as the reflected light with a CCD camera.

In the inspection of the conductive pattern 41 described in Japanese Unexamined Patent No. 2006-112845, the difference between an amount of the pattern reflected light 51 and an amount of the table reflected light 52, i.e., the contrast (brightness difference) therebetween is used to recognize the shape of the conductive pattern 41, and determine whether or not the shape of the conductive pattern 41 is defective.

In the inspection of Japanese Unexamined Patent No. 2006-112845, there is the problem that, when the contrast between the pattern reflected light 51 and the table reflected light 52 is low, the shape of the conductive pattern 41 is difficult to recognize. To solve such a problem, it has been proposed that the reflectance of the table reflected light 52 is reduced to a value of not more than 10% to ensure a high contrast between the pattern reflected light 51 and the table reflected light 52.

On the other hand, it has been conventionally proposed that, in the production of a wired circuit board, a foreign matter present on a conductive pattern is inspected (see, e.g., Japanese Unexamined Patent No. 11-307883).

Specifically, as indicated by the solid line of FIG. 5, the reflectance of foreign-matter reflected light 53 which is the light reflected by a foreign matter 46 is low when the foreign matter 46 is made of a resin material such as rubber. Accordingly, the foreign matter 46 present on the conductive pattern 41 is inspected by ensuring a high contrast between the foreign-matter reflected light 53 and the pattern reflected light 51.

SUMMARY OF THE INVENTION

However, as indicated by the phantom lines of FIG. 5, when the foreign matter 46 is present on the insulating base layer 42 exposed from the conductive pattern 41, each of the foreign-matter reflected light 53 and the table reflected light 52 has a low reflectance so that the contrast therebetween is low. As a result, it is difficult to inspect the foreign matter 46 present on the insulating base layer 42 exposed from the conductive pattern 41.

It is therefore an object of the present invention to provide a producing method of a wired circuit board which allows an inspection of a conductive pattern and an inspection of a foreign matter present on an insulating layer exposed from the conductive pattern to be performed easily and simultaneously.

A producing method of a wired circuit board of the present invention includes preparing the wired circuit board comprising an insulating layer, and a conductive pattern formed on the insulating layer, placing the wired circuit board on a support table, and applying light from above the wired circuit board toward the wired circuit board, and sensing pattern reflected light which is the light reflected by the conductive pattern, table reflected light which is the light reflected by the support table via the insulating layer exposed from the conductive pattern, and foreign-matter reflected light which is the light reflected by a foreign matter present on the insulating layer exposed from the conductive pattern to inspect the conductive pattern and the foreign matter based on a contrast therebetween, wherein, in the step of inspecting the conductive pattern and the foreign matter, a reflectance of the table reflected light is in a range of 30 to 70%, and a reflectance of the foreign-matter reflected light is in a range of not more than 10%.

In the producing method of the wired circuit board of the present invention, it is preferable that a reflectance of the pattern reflected light is higher than the reflectance of the table reflected light by a value of not less than 20%.

In the producing method of the wired circuit board of the present invention, it is also preferable that a wavelength of the light is in a range of not less than 500 nm.

In accordance with the producing method of the wired circuit board of the present invention, in the step of inspecting the conductive pattern and the foreign matter, the reflectance of the table reflected light is in the range of 30 to 70%, and the reflectance of the foreign-matter reflected light is in the range of not more than 10%.

This allows each of the contrast between the pattern reflected light and the table reflected light and the contrast between the table reflected light and the foreign-matter reflected light to be set high in a well-balanced manner.

Therefore, it is possible to easily and simultaneously perform an inspection of the conductive pattern and an inspection of the foreign matter present on the insulating layer exposed from the conductive pattern.

BRIEF DESCRIPTION OF THE DRAWINGS

FIG. 9 shows an image processed view in an inspection step of COMPARATIVE EXAMPLE 1;

FIG. 10 shows an image processed view in an inspection step of COMPARATIVE EXAMPLE 2;

FIG. 11 shows an image processed view in an inspection step of COMPARATIVE EXAMPLE 3; and FIG. 12 shows an image processed view in an inspection step of COMPARATIVE EXAMPLE 4.

DETAILED DESCRIPTION OF THE INVENTION

Figure 1:
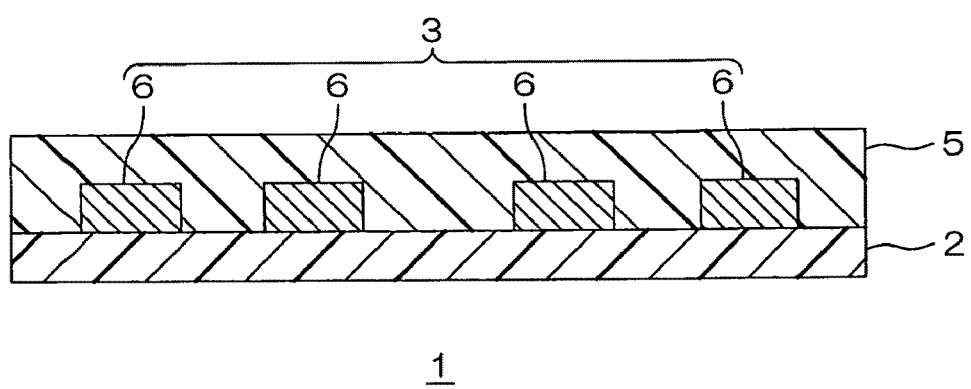
FIG. 1 is a cross-sectional view along a widthwise direction of an embodiment of a wired circuit board produced by a producing method of a wired circuit board of the present invention.
Figure 2:
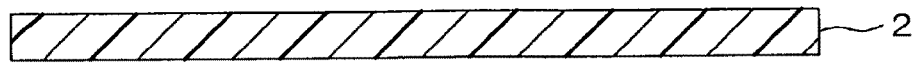
FIG. 2 is a process step view of an embodiment of the producing method of the wired circuit board of the present invention, (a) showing the step of preparing an insulating base layer, (b) showing the step of forming a conductive pattern, (c) showing the step of inspecting the conductive pattern and a foreign matter in the wired circuit board in which a foreign matter is not present, and wires are formed normally, or (c') showing the step of inspecting the conductive pattern and a foreign matter in the wired circuit board in which the foreign matter is present, and wires are short-circuited, and (d) showing the step of forming an insulating cover layer.
Figure 2:
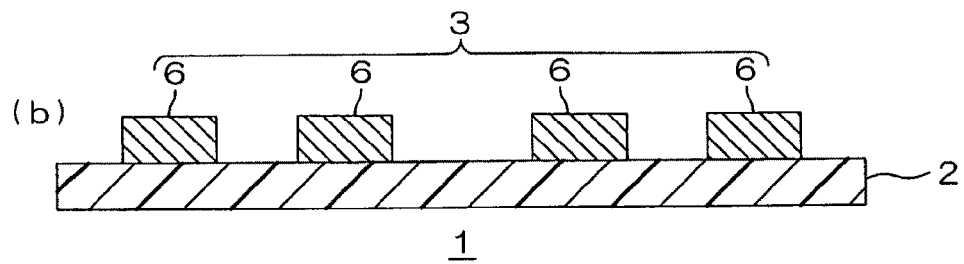
Figure 2:
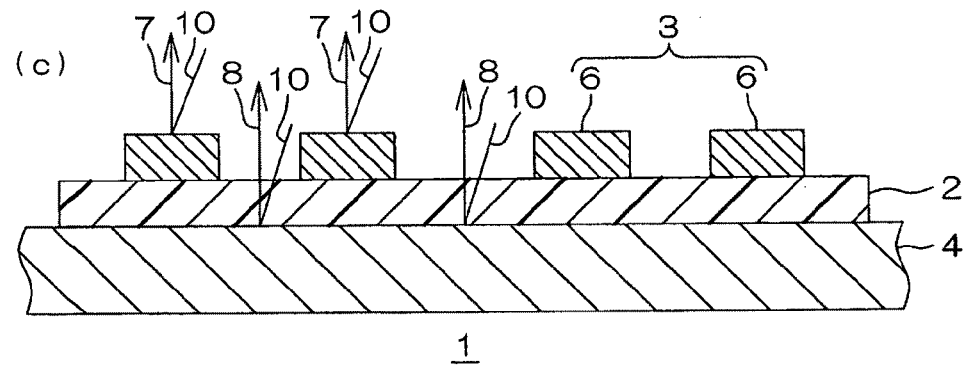
Figure 2:
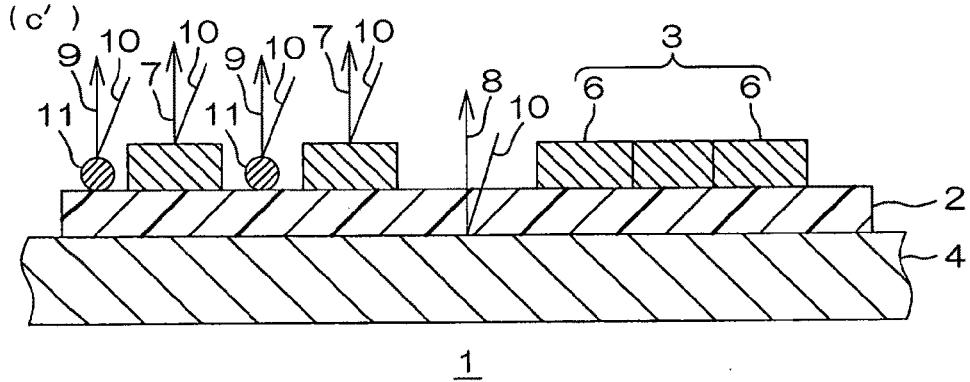
Figure 2:
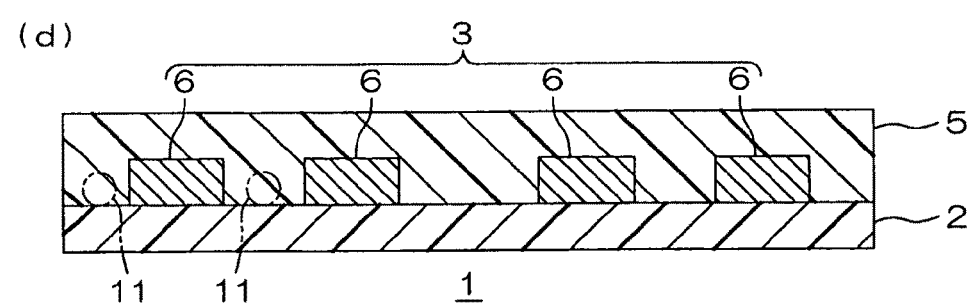
Figure 3:
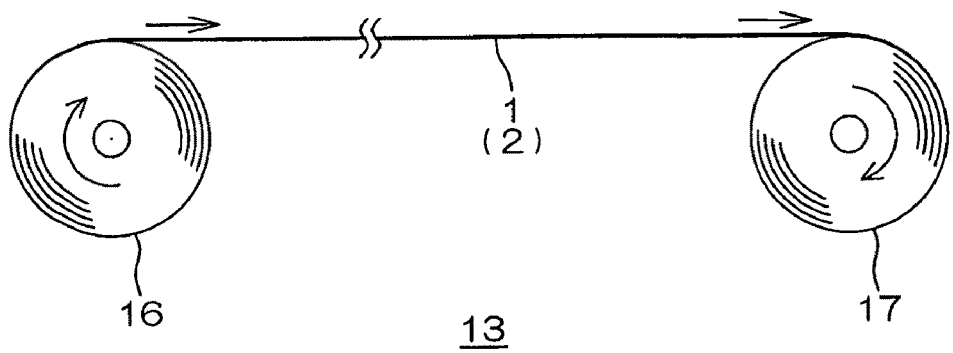
FIG. 3 is a schematic structural view of a conveying device for implementing the embodiment of FIG. 2.
Figure 4:
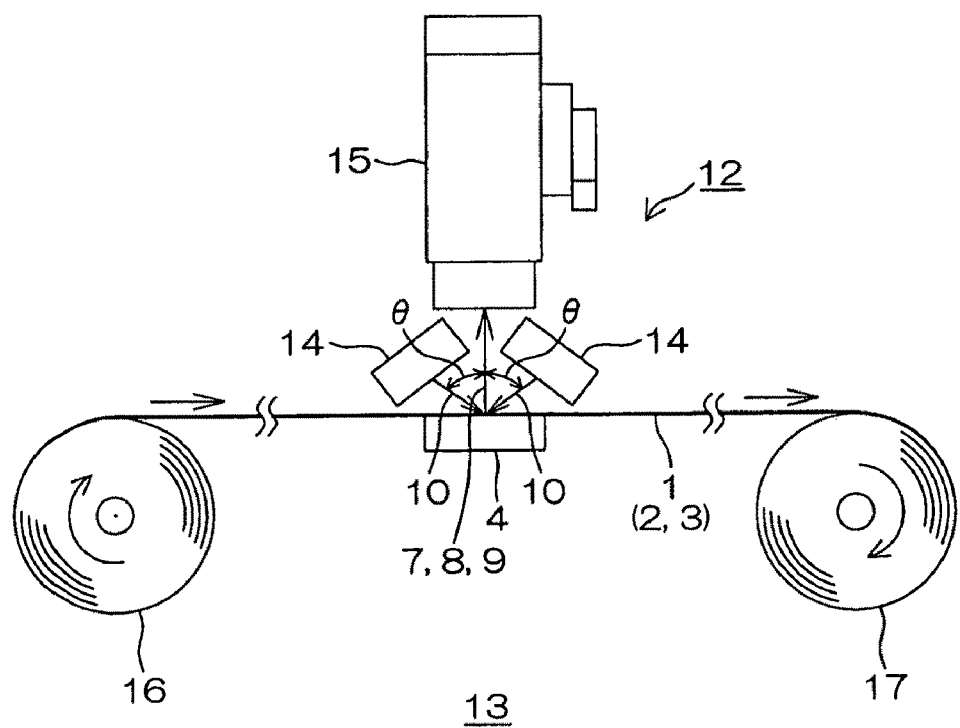
FIG. 4 is a schematic structural view of an inspection device for performing an inspection step.
Figure 5:
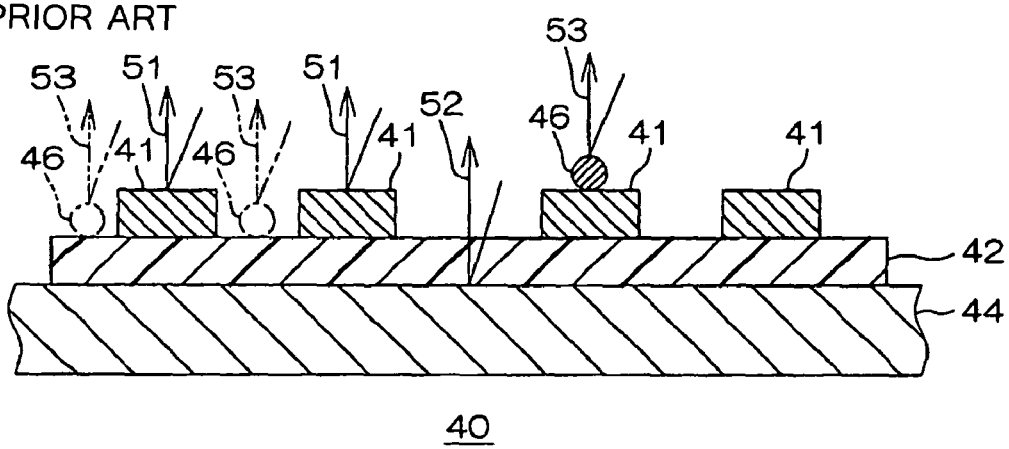
FIG. 5 is an illustrative view of a prior-art technology, showing the step of inspecting a wired circuit board in which a foreign matter is present on a conductive pattern.

FIG. 1 is a cross-sectional view along a widthwise direction (direction perpendicular to a longitudinal direction) of an embodiment of a wired circuit board produced by a producing method of a wired circuit board of the present invention. FIG. 2 is a process step view of an embodiment of the producing method of the wired circuit board of the present invention. FIG. 3 is a schematic structural view of a conveying device for implementing the embodiment of FIG. 2. FIG. 4 is a schematic structural view of an inspection device for performing an inspection step described later.

In FIG. 1, a wired circuit board 1 is a flexible wired circuit board formed in a flat-belt sheet-like shape extending in the longitudinal direction. The wired circuit board 1 includes an insulating base layer 2 as an insulating layer, and a conductive pattern 3 formed on the insulating base layer 2. As necessary, the wired circuit board 1 also includes an insulating cover layer 5 formed on the insulating base layer 2 so as to cover the conductive pattern 3.

Examples of an insulating material used to form the insulating base layer 2 include synthetic resins such as polyimide, polyamideimide, acryl, polyether nitrile, polyether sulfone, polyethylene terephthalate (PET), polyethylene naphthalate, and polyvinyl chloride. Preferably, in terms of heat resistance and a light transmission characteristic, polyimide is used.

As necessary, a pigment or the like is mixed in the insulating material shown above. The pigment is mixed in a proper proportion so as to adjust the reflectance R2 of table reflected light 8 in an inspection step described later.

The insulating base layer 2 is formed in a flat-belt sheet-like shape correspondingly to the outer shape of the wired circuit board 1 extending in the longitudinal direction.

The insulating base layer 2 has a light transmittance T in a range of, e.g., not less than 60%, preferably not less than 70%, or more preferably not less than 80%, and normally not more than 100% with respect to light at a wavelength in a range of not less than 500 nm (in a range of preferably 500 to 1500 nm, or more preferably 500 to 1000 nm).

The thickness of the insulating base layer 2 is in a range of, e.g., 5 to 50 μm, or preferably 10 to 40 μm.

Examples of a conductive material used to form the conductive pattern 3 include conductive materials such as copper, nickel, gold, a solder, and an alloy thereof. Preferably, in terms of electric resistance and a light reflection characteristic, copper is used.

The conductive pattern 3 integrally includes wires 6 extending along the longitudinal direction, and arranged in parallel to be spaced apart from each other in the widthwise direction, and terminal portions not shown, but disposed at the both longitudinal end portions of each of the wires 6. Each of the wires 6 is covered with the insulating cover layer 5, while each of the terminal portions not shown is exposed from the insulating cover layer 5. The conductive pattern 3 is formed in a generally rectangular cross-sectional (widthwise cross-sectional) shape.

The thickness of the conductive pattern 3 is in a range of, e.g., 3 to 30 μm, or preferably 5 to 20 μm. The respective widths (widthwise lengths) of the wires 6 and the terminal portions may be the same or different from each other, and are in a range of, e.g., 5 to 500 μm, or preferably 15 to 200 μm. The respective spacings (widthwise spacings) between the individual wires 6 and between the individual terminal portions may be the same or different from each other, and are in a range of, e.g., 5 to 200 μm, or preferably 5 to 100 μm.

The insulating cover layer 5 covers and electrically seals the wires 6. As an insulating material for forming the insulating cover layer 5, the same insulating material as used to form the insulating base layer 2 shown above is used.

The insulating cover layer 5 is formed on the surface of the insulating base layer 2 into a pattern covering the wires 6, and exposing the terminal portions. The thickness of the insulating cover layer 5 is in a range of, e.g., 10 to 50 μm, or preferably 14 to 20 μm.

Next, an embodiment of the producing method of the wired circuit board of the present invention is described with reference to FIGS. 2 to 4.

In the method, as shown in FIG. 3, each of the steps (FIGS. 2(a) to 2(d)) in the production of the wired circuit board 1 is performed by, e.g., a roll-to-roll method using a conveying device 13. For example, the conveying device 13 includes a feed-out roll 16 and a wind-up roll 17 which are disposed in mutually spaced-apart relation.

In the roll-to-roll method, e.g., the elongated insulating base layer 2 wound in a roll around the feed-out roll 16 is carried by roll-to-roll conveyance in such a manner as to be fed out toward the wind-up roll 17, and wound up by the wind-up roll 17 for each of the steps. In the course of the roll-to-roll conveyance, the individual steps shown in FIG. 2 are performed in succession.

First, in the method, as shown in FIG. 2(a), the insulating base layer 2 is prepared as a sheet wound around the feed-out roll 16.

Next, in the method, as shown in FIG. 2(b), the conductive pattern 3 is formed in a wired circuit pattern having the wires 6 and the terminal portions on the insulating base layer 2. The conductive pattern 3 is formed by, e.g., a known patterning method such as a subtractive method or an additive method.

In this manner, the wired circuit board 1 (wired circuit board 1 prior to the inspection step) including the insulating base layer 2 and the conductive pattern 3 formed thereon is prepared.

Thereafter, as shown in FIG. 2(c) or 2(c'), the wired circuit board 1 is disposed on a support table 4 (described later), and then the conductive pattern 3 and a foreign matter 11 are inspected (inspection step). In the inspection step, an inspection device 12 shown in FIG. 4 is used.

The inspection device 12 is disposed between the feed-out roll 16 and the wind-up roll 17. The inspection device 12 includes light emitting units 14 and a light receiving unit 15 which are disposed above the wired circuit board 1 conveyed between the feed-out roll 16 and the wind-up roll 17 in the thickness direction of the wired circuit board 1, and also includes the support table 4 disposed below the light emitting units 14 and the light receiving unit 15 in the thickness direction in facing relation thereto.

The light emitting units 14 are disposed in spaced-apart and facing relation in a direction of conveyance. The lower surface of each of the light emitting units 14 facing the wired circuit board 1 serves as a light emitting surface from which a beam of light 10 is emitted. To cause the beams of light 10 emitted from the respective light emitting surfaces to be condensed onto the wired circuit board 1 at a midpoint between the individual light emitting units 14, the light emitting units 14 are disposed in line symmetry to be tilted around a portion where the light beams are condensed (around a condensed light line along the widthwise direction of the wired circuit board 1).

Specifically, each of the light emitting units 14 is a lamp capable of emitting the beam of light 10 at a wavelength in a range of not less than 500 nm (preferably 500 to 1500 nm, or more preferably 500 to 1000 nm). Preferably, as a light source, a near infrared LED (light emitting diode) capable of emitting light in a wavelength range including those shown above is used.

When the wavelength of the light 10 is within the range shown above, it is possible to ensure a high light transmittance of the insulating base layer 2, and set the reflectance R2 (described later) of the table reflected light 8 to a value within a desired range in the inspection step. This allows better-balanced setting of the contrast (described later) between pattern reflected light 7 and the table reflected light 8 and the contrast (described later) between the table reflected light 8 and foreign-matter reflected light 9.

The light receiving unit 15 is disposed above the wired circuit board 1 in the thickness direction to be spaced-apart therefrom, and disposed between the individual light emitting units 14 in the direction of conveyance. The lower surface of the light receiving unit 15 serves as a light receiving surface which receives beams of the reflected light 7, 8, and 9 (described later). The light receiving surface of the light receiving unit 15 is disposed above the light emitting units 14 so as to face the portion where the light beams are condensed from thereabove.

Specifically, the light receiving unit 15 is formed of, e.g., a near infrared camera, a CCD camera, or the like. Preferably, in terms of versatility, the light receiving unit 15 is formed of a CCD camera, more specifically a CCD line scan camera capable to reading a line (condensed light line) perpendicular to the direction of conveyance of the wired circuit board 1.

The support table 4 has a generally flat-plate shape, and an upper surface thereof (top surface) formed as a flat smooth surface. To set the reflectance R2 of the table reflected light 8 described later to a value within a desired range, a metal material such as, e.g., stainless steel (specifically SUS304 or the like) or aluminum, a fluorine-containing resin material such as, e.g., polytetrafluoroethylene, or the like is used as a material for forming the support table 4. As necessary, a metal film is formed on the upper surface of the support table 4.

As an example of a material for forming the metal film, the same metal material as used to form the support table 4 shown above is used. As a material for forming the metal film and a metal material for forming the support table 4, different kinds of materials are typically used in combination. The thickness of the metal film is in a range of, e.g., 0.1 to 100 µm.

The support table 4 is disposed below the wired circuit board 1 to be conveyed. The support table 4 has an upper surface thereof in slidable contact with the lower surface of the wired circuit board 1, thereby supporting the wired circuit board 1. The support table 4 is formed with a through hole extending therethrough in the thickness direction, though not shown. To the lower end of the through hole, a compressor is connected.

In the inspection device 12, the angle θ formed between each of the beams of irradiation light 10 emitted from the light emitting units 14 and the reflected light received by the light receiving unit 15 is set to a range of, e.g., 0 to 90 degrees, or preferably 0 to 45 degrees. The distance between the light emitting surface of each of the light emitting units 14 and the portion of the wired circuit board 1 where the light beams are condensed is set to a range of, e.g., 5 to 300 mm, or preferably 10 to 100 mm. The distance between the portion of the wired circuit board 1 where the light beams are condensed and the light receiving surface of the light receiving unit 15 is set to a range of, e.g., 20 to 300 mm.

Then, by feeding out the wired circuit board 1 wound around the feed-out roll 16 toward the wind-up roll 17 such that the lower surface of the insulating base layer 2 comes into contact with the upper surface of the support table 4, the wired circuit board 1 is placed on the support table 4.

Thereafter, the feed-out operation by the feed-out roll 16 and the wind-up operation by the wind-up roll 17 are interrupted. Then, by activating the compressor to suck in air via the through hole, the wired circuit board 1 is fixed onto the support table 4 (attracted thereto by suction).

Subsequently, the conductive pattern 3 and the foreign matter 11 in the wired circuit board 1 are simultaneously inspected with the inspection device 12.

In the inspection step, the beams of light (irradiation light) 10 at the wavelengths shown above are applied to the wired circuit board 1 from thereabove. Specifically, the beams of light 10 at the wavelengths shown above are emitted from the light emitting units 14 toward the wired circuit board 1.

Through the application of the foregoing light 10, as shown in FIGS. 2(c) and 2(c'), the pattern reflected light 7 which is the foregoing light 10 reflected by the surface of the conductive pattern 3, the table reflected light 8 which is the foregoing light 10 reflected by the support table 4 via the insulating base layer 2 (insulating base layer 2 between the individual portions of the conductive pattern 3) exposed from the conductive pattern 3, and the foreign-matter reflected light 9 (described later) which is the foregoing light 10 reflected by the foreign matter 11 are sensed by the light receiving unit 15.

A reflectance R1 of the pattern reflected light 7 is in a range of, e.g., not less than 70%, preferably not less than 80%, or more preferably not less than 90%, and normally not more than 100%.

The reflectance R1 of the pattern reflected light 7 is obtained as the ratio (=Amount of Pattern Reflected Light 7)/(Amount of Irradiation Light 10)×100) of an amount of the pattern reflected light 7 sensed by the light receiving unit 15 to an amount of the irradiation light 10 emitted from the light emitting units 14 when the amount of the irradiation light 10 is assumed to be 100%.

The table reflected light 8 contains, as a primary component thereof, light which is the irradiation light 10 incident on the upper surface of the insulating base layer 2, downwardly passed through the inside of the insulating base layer 2, reflected by the upper surface of the support table 4, upwardly passed through the inside of the insulating base layer 2 again, and then emitted from the upper surface of the insulating base layer 2. The table reflected light 8 also contains, as a secondary component thereof, light (not shown) which is the irradiation light 10 reflected by the upper surface of the insulating base layer 2.

The reflectance R2 of such table reflected light 8 is in a range of 30 to 70%, preferably 30 to 60%, or more preferably 30 to 50%.

The reflectance R2 of the table reflected light 8 is obtained as the ratio ((Amount of Table Reflected Light 8)/(Amount of Irradiation Light 10)×100) of an amount of the table reflected light 8 sensed by the light receiving unit 15 to the amount of the irradiation light 10 emitted from the light emitting units 14 when the amount of the irradiation light 10 is assumed to be 100%.

A reflectance R3 of the foreign-matter reflected light 9 is determined by a material forming the foreign matter 11 described later, and is in a range of, e.g., not more than 10%, preferably not more than 5%, or more preferably not more than 1%, and normally not less than 0.2%.

The reflectance R3 of the foreign-matter reflected light 9 is obtained as the ratio ((Amount of Foreign-Matter Reflected Light 9)/(Amount of Irradiation Light 10)×100) of an amount of the foreign-matter reflected light 9 sensed by the light receiving unit 15 to the amount of the irradiation light 10 emitted from the light emitting units 14 when the amount of the irradiation light 10 is assumed to be 100%.

As shown in FIG. 2($c'$), the foreign matter 11 is present on the insulating base layer 2 exposed from the conductive pattern 3 in the wired circuit board 1 which is determined to be a defective product. Specifically, the foreign matter 11 is present between the individual portions of the conductive pattern 3 (between the individual wires 6 adjacent in the widthwise direction) or present widthwise outside the conductive pattern 3 (outside the widthwise outermost wires 6).

The shape of the foreign matter 11 is not particularly limited. A material for forming the foreign matter 11 is not particularly limited as long as the reflectance R3 shown above is satisfied thereby. Examples of the material that can be listed include a carbon-based inorganic material (a conductive inorganic material except for a metal material) such as carbon black, carbon nanotube, carbon fiber, or graphite, and an organic material (resin material) such as rubber or an adhesive.

In particular, when the foreign matter 11 formed of a material which impairs the performance (electric signal transmission performance) of the conductive pattern 3 is contained, it is necessary to reliably determine the wired circuit board 1 to be a defective product, and remove the wired circuit board 1 or adds a mark (mark indicative of a defective product) thereto. Accordingly, as a material for forming the foreign matter 11 to be sensed, a conductive inorganic material (except for a metal material) can be particularly listed.

Then, based on the contrast (difference between the amounts of light) between the sensed beams of reflected light 7, 8, and 9, the conductive pattern 3 and the foreign matter 11 are simultaneously inspected.

That is, the respective amounts of the beams of reflected light 7, 8, and 9 that have been sensed by the light receiving unit 15 are each subjected to data processing using a CPU (not shown) connected to the light receiving unit 15 or the like to form image processed views (image processed views obtained when the wired circuit board 1 is viewed in plan view. See FIGS. 6 to 8). In the formed image processed views, the conductive pattern 3, the insulating base layer 2, and the foreign matter 11 are depicted, and thereby inspected.

Specifically, as shown in FIGS. 2($c$), 2($c'$), and 6 to 8, the conductive pattern 3 is inspected based on the contrast between the pattern reflected light 7 and the table pattern light 8.

In the inspection of the conductive pattern 3, pattern data of the conductive pattern 3 is acquired from the contrast between the pattern reflected light 7 and the table reflected light 8, and image processed views are formed using the CPU. From such image processed views, the pattern shape of the conductive pattern 3 is correctly recognized so that a defect in the wires 6 or the terminal portions, a short circuit between the wires 6 or between the terminal portions, and the like are accurately determined.

The contrast between the pattern reflected light 7 and the table reflected light 8 is a difference D1 between the respective reflectances thereof and, more specifically, the value D1 (=R1−R2) obtained by subtracting the reflectance R2 of the table reflected light 8 from the reflectance R1 of the pattern reflected light 7, which is in a range of, e.g., not less than 20%, or preferably not less than 30%, and normally not more than 70%. In other words, the reflectance R1 of the pattern reflected light 7 is higher than the reflectance R2 of the table reflected light 8 by a value of, e.g., not less than 20%, or preferably not less than 30%.

When the contrast between the pattern reflected light 7 and the table reflected light 8 is within the range shown above, it is possible to more accurately determine whether or not the shape of the conductive pattern 3 is defective.

In the inspection of the conductive pattern 3 described above, when the pattern data acquired from the contrast between the pattern reflected light 7 and the table reflected light 8 is acquired as pattern data which is not present in the pattern data of the conductive pattern 3 as shown in FIG. 2($c'$), it is determined that the shape of the conductive pattern 3 is defective (the wires 6 are short-circuited). On the other hand, when there is no difference between the pattern data acquired from the contrast between the pattern reflected light 7 and the table reflected light 8 and the original pattern data of the conductive pattern 3 as shown in FIG. 2($c$), it is determined that the shape of the conductive pattern 3 is normal.

As shown in FIGS. 2($c'$), and 6 to 8, the foreign matter 11 is inspected based on the contrast between the table reflected light 8 and the foreign-matter reflected light 9.

In the inspection of the foreign matter 11, pattern data of the insulating base layer 2 exposed from the conductive pattern 3 is acquired from the contrast between the table reflected light 8 and the foreign-matter reflected light 9, and an image processed view is formed using the CPU. From such an image processed view, the pattern shape of the insulating base layer 2 exposed from the conductive pattern 3 is correctly recognized, and the presence or absence of the foreign matter 11 is accurately determined.

The contrast between the table reflected light 8 and the foreign-matter reflected light 9 is the difference D2 between the respective reflectances thereof and, more specifically, a value D2 (=R2−R3) obtained by subtracting the reflectance R3 of the foreign-matter reflected light 9 from the reflectance R2 of the table reflected light 8, which is in a range of, e.g., not less than 20%, preferably not less than 30%, and normally not more than 70%. In other words, the reflectance R2 of the table reflected light 8 is higher than the reflectance R3 of the foreign-matter reflected light 9 by a value of, e.g., not less than 20%, or preferably not less than 30%.

In the inspection of the foreign matter 11 described above, when the pattern data acquired from the contrast between the table reflected light 8 and the foreign-matter reflected light 9 is obtained as pattern data which is not present in the pattern data of the insulating base layer 2 exposed from the conductive pattern 3 as shown in FIG. 2(c'), it is determined that the foreign matter 11 is present on the insulating base layer 2 exposed from the conductive pattern 3. On the other hand, when there is no difference between the pattern data acquired from the contrast between the table reflected light 8 and the foreign-matter reflected light 9 and the original pattern data of the insulating base layer 2 exposed from the conductive pattern 3, it is determined that the foreign matter 11 is not present on the insulating base layer 2 exposed from the conductive pattern 3.

Note that the inspection using the beams of light 10 at the wavelengths shown above is typically performed at a room temperature (25° C.), and the temperature of the surface (the surfaces of the insulating base layer 2 and the conductive pattern 3) of the wired circuit board 1 after the inspection is, e.g., a room temperature, not more than 30° C., or preferably not more than 25° C. That is, the range of temperature rise observed after the inspection of the conductive pattern 3 and the foreign matter 11 is, e.g., not more than 5° C.

Subsequently, in the method, the suction by the compressor is terminated to unfix the wired circuit board 1 from the support table 4, and then the conveyance of the wired circuit board 1 by the conveying device 13 is resumed. As a result, the wired circuit board 1 after the inspection step is wound up by the wind-up roll 17, while the wired circuit board 1 prior to the inspection step 1 is newly fed out from the feed-out roll 16, placed on the support table 4, and fixed thereto. Thereafter, the same inspection step as described above is performed. In the inspection device 12, such an inspection step is repeated.

Then, in the method, as shown in FIG. 2(d), the insulating cover layer 5 is formed in the foregoing pattern on the insulating base layer 2 so as to cover the conductive pattern 3.

The formation of the insulating cover layer 5 is performed by a known method such as, e.g., coating with a resin solution, or sticking of a resin sheet.

In the coating with a resin solution, for example, a photosensitive resin solution (varnish) containing a solution of the synthetic resin shown above and a photosensitive agent is prepared first. The photosensitive varnish is coated on the entire upper surface of the insulating base layer 2 including the conductive pattern 3, and dried to form a cover coating. Then, the cover coating is exposed to light via a photomask, and developed to be processed into a pattern, and cured by heating as necessary.

In the sticking of a resin sheet, a sheet of an insulating material (containing a pigment as necessary) formed into the foregoing pattern in advance is laminated onto the insulating base layer 2 and the conductive pattern 3 via a known adhesive.

Thereafter, the wired circuit board 1 wound up by the wind-up roll 17, and determined to be a defective product is removed by cutting it off from the elongated insulating base layer 2 or marked, while the wired circuit board 1 determined to be a non-defective product is produced.

In accordance with the method, in the inspection step for the conductive pattern 3 and the foreign matter 11, the reflectance R2 of the table reflected light 8 is in a range of 30 to 70%, the reflectance R3 of the foreign-matter reflected light 9 is in a range of not more than 10%.

This allows each of the contrast between the pattern reflected light 7 and the table reflected light 8 and the contrast between the table reflected light 8 and the foreign-matter reflected light 9 to be set high in a well-balanced manner.

Therefore, it is possible to easily and simultaneously perform the inspection of the conductive pattern 3 and the inspection of the foreign matter 11 present on the insulating base layer 2 exposed from the conductive pattern 3.

In the description given above, the roll-to-roll method has been shown as an example of the producing method of the wired circuit board of the present invention. However, the producing method of the wired circuit board of the present invention is not limited thereto. For example, it is possible to use a single-wafer method or the like, though not shown.

In the description given above, the flexible wired circuit board in which the insulating base layer 2 is not supported by a metal supporting layer or the like is shown as an example of the wired circuit board obtained by the producing method of the wired circuit board of the present invention. However, the producing method of the wired circuit board of the present invention is widely applicable to the production of various wired circuit boards such as a flexible wired circuit board in which the lower surface of the peripheral end portion of the insulating base layer 2 is supported by a metal supporting layer, and the metal supporting layer is provided as a reinforcing layer, a COF board (including a TAB tape carrier or the like), and a suspension board with circuit.

EXAMPLES

Hereinbelow, the present invention is described more specifically by showing the examples and comparative examples thereof. However, the present invention is by no means limited to the examples and the comparative examples.

Example 1

By a roll-to-roll method using the conveying device shown in FIG. 3 described above, the following steps were performed in succession to produce a flexible wired circuit board.

That is, an insulating base layer made of polyimide and in the shape of an elongated sheet having a width of 300 mm and a thickness of 25 μm was prepared (see FIG. 2(a)).

Then, on the insulating base layer, a conductive pattern made of copper and having a thickness of 8 μm was formed in a wired circuit pattern having wires and terminal portions by an additive method (see FIG. 2(b)). The width of each of the wires was 30 μm. The width of each of the terminal portions was 30 μm. The spacing between the individual wires was 60 μm. The widthwise spacing between the individual terminal portions was 60 μm.

Then, carbon black (foreign matter) having an average particle diameter of 20 μm was mixed onto the insulating base layer exposed from the wires.

Then, as shown in FIG. 4 described above, the carbon black and the conductive pattern were simultaneously inspected using an inspection device including light emitting units (light sources: near infrared LEDs for diffused illumination), a light receiving unit (CCD line scan camera, Model No. P3-80-12K40 commercially available from DALSA, Inc.), and a support table (made of stainless steel (SUS304)) (see FIGS. 2(c) and 2(c')).

In the inspection device, the angle formed between a light beam emitted from each of the light emitting units and light received by the light receiving unit was 10 degrees, the distance between the light emitting surface of each of the light emitting units and the portion of the flexible wired circuit board where the light beams were condensed was 50 mm, and the distance between the light receiving surface of the light receiving unit and the portion of the flexible wired circuit board where the light beams were condensed was 120 mm.

This inspection was performed using light at a wavelength of 850 nm at a temperature of 25° C.

Figure 6:
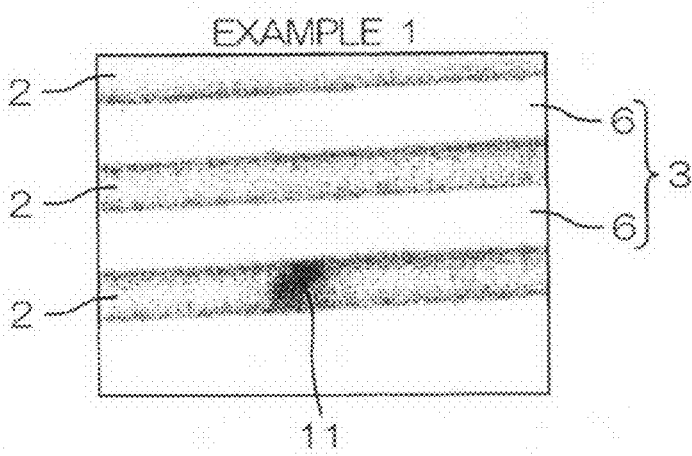
FIG. 6 shows an image processed view in an inspection step of EXAMPLE 1.

An image processed view obtained by data processing is shown in FIG. 6, and evaluation in the inspection is shown in Table 1.

Thereafter, a varnish of a photosensitive polyamic acid resin was coated on the conductive pattern and the insulating base layer including the foreign matter, dried, exposed to light, developed to be processed into the foregoing pattern, and then cured by heating to form an insulating cover layer made of polyimide and having a thickness of 18 μm (see FIG. 2(*d*)).

Example 2

An inspection step was performed in the same manner as in EXAMPLE 1 except that a support table (made of stainless steel) having a surface thereof formed with a tin film having a thickness of 0.5 μm was used in the inspection step.

Figure 7:
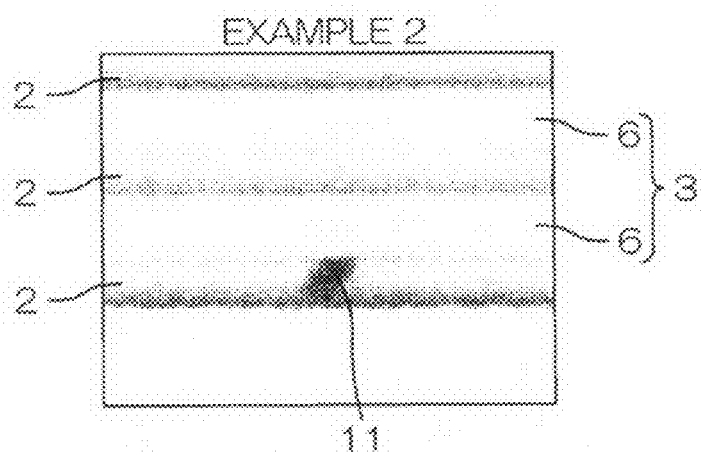
FIG. 7 shows an image processed view in an inspection step of EXAMPLE 2.

An image processed view obtained by data processing is shown in FIG. 7, and evaluation in the inspection is shown in Table 1.

Example 3

An inspection step was performed in the same manner as in EXAMPLE 1 except that a support table (made of stainless steel) having a surface thereof formed with a nickel film having a thickness of 2 μm was used in the inspection step.

Figure 8:
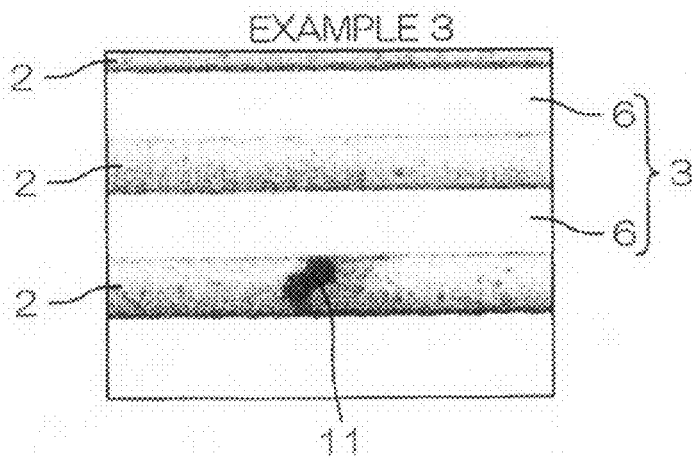
FIG. 8 shows an image processed view in an inspection step of EXAMPLE 3.

An image processed view obtained by data processing is shown in FIG. 8, and evaluation in the inspection is shown in Table 1.

Comparative Example 1

An inspection step was performed in the same manner as in EXAMPLE 1 except that a support table (made of stainless steel) having a surface thereof formed with a copper film having a thickness of 8 μm was used in the inspection step.

An image processed view obtained by data processing is shown in FIG. 9, and evaluation in the inspection is shown in Table 1.

Comparative Example 2

An inspection step was performed in the same manner as in EXAMPLE 1 except that a support table (made of stainless steel) having a surface thereof to which a black tape made of a vinyl chloride resin and having a thickness of 500 μm had been sticked was used in the inspection step.

An image processed view obtained by data processing is shown in FIG. 10, and evaluation in the inspection is shown in Table 1.

Comparative Example 3

A wired circuit board was produced, and an inspection step was subsequently performed in the same manner as in EXAMPLE 1 except that a tin plating layer having a thickness of 0.5 μm was further formed on the surface of the conductive pattern in the step of forming the conductive pattern, and a support table (made of stainless steel) having a surface thereof formed with a copper film having a thickness of 8 μm was used in the inspection step.

An image processed view obtained by data processing is shown in FIG. 11, and evaluation in the inspection is shown in Table 1.

Comparative Example 4

An inspection step was performed in the same manner as in EXAMPLE 1 except that a tin plating layer having a thickness of 0.5 μm was further formed on the surface of the conductive pattern in the step of forming the conductive pattern, and a support table (made of stainless steel) having a surface thereof to which a black tape made of a vinyl chloride resin and having a thickness of 500 μm had been sticked was used in the inspection step.

An image processed view obtained by data processing is shown in FIG. 12, and evaluation in the inspection is shown in Table 1.

TABLE 1

|  |  | Examples/Comparative Examples | | | | | | |
|---|---|---|---|---|---|---|---|---|
|  |  | Example 1 | Example 2 | Example 3 | Comparative Example 1 | Comparative Example 2 | Comparative Example 3 | Comparative Example 4 |
| Material | Surface of Conductive Pattern | Copper | Copper | Copper | Copper | Copper | Tin | Tin |
|  | Surface of Support Table | Stainless Steel | Tin | Nickel | Copper | Tape Made of Polyvinyl Chloride Resin (Black) | Copper | Tape Made of Polyvinyl Chloride Resin (Black) |
| Reflectance (%) | Pattern Reflected Light (R1) | 90 | 90 | 90 | 90 | 90 | 65 | 65 |
|  | Table Reflected Light (R2) | 50 | 70 | 35 | 80 | 10≦ | 80 | 10≦ |
|  | Foreign-Matter Reflected Light (R3) | 10≦ | 10≦ | 10≦ | 10≦ | 10≦ | 10≦ | 10≦ |

TABLE 1-continued

| | | Examples/Comparative Examples | | | | | | |
|---|---|---|---|---|---|---|---|---|
| | | Example 1 | Example 2 | Example 3 | Comparative Example 1 | Comparative Example 2 | Comparative Example 3 | Comparative Example 4 |
| Inspection | Foreign Matter | Successfully Inspected | Successfully Inspected | Successfully Inspected | Successfully Inspected | Unsuccessfully Inspected | Successfully Inspected | Unsuccessfully Inspected |
| | Conductive Pattern | Successfully Inspected | Successfully Inspected | Successfully Inspected | Unsuccessfully Inspected | Successfully Inspected | Unsuccessfully Inspected | Unsuccessfully Inspected |

In the row showing the results of the inspections of the foreign matter of Table 1, "Successfully Inspected" indicates that the presence of the foreign matter could be definitely determined, and "Unsuccessfully Inspected" indicates that the presence or absence of the foreign matter could not be definitely determined. In the row showing the results of the inspections of the conductive pattern, "Successfully Inspected" indicates that the normal shape of the conductive pattern could be definitely determined, and "Unsuccessfully Inspected" indicates that whether or not the shape of the conductive pattern was defective could not be determined.

While the illustrative embodiments of the present invention are provided in the above description, such is for illustrative purpose only and it is not to be construed limitative. Modification and variation of the present invention that will be obvious to those skilled in the art is to be covered by the following claims.

What is claimed is:

1. A producing method of a wired circuit board, the producing method comprising the steps of:
preparing the wired circuit board comprising an insulating layer, and a conductive pattern formed on the insulating layer;
placing the wired circuit board on a support table; and
applying light from above the wired circuit board toward the wired circuit board using an inspection device comprising at least one light emitting unit and at least one light receiving unit, and sensing pattern reflected light which is the light reflected by the conductive pattern, table reflected light which is the light reflected by the support table via the insulating layer exposed from the conductive pattern, and foreign-matter reflected light which is the light reflected by a foreign matter present on the insulating layer exposed from the conductive pattern to inspect the conductive pattern and the foreign matter based on a contrast therebetween, wherein,
in the step of inspecting the conductive pattern and the foreign matter, a reflectance of the table reflected light is in a range of 30 to 70%, and a reflectance of the foreign-matter reflected light is in a range of not more than 10%.

2. The producing method of the wired circuit board according to claim 1, wherein a reflectance of the pattern reflected light is higher than the reflectance of the table reflected light by a value of not less than 20%.

3. The producing method of the wired circuit board according to claim 1, wherein a wavelength of the light is in a range of not less than 500 nm.

* * * * *